(12) United States Patent
Bergström et al.

(10) Patent No.: US 8,283,292 B2
(45) Date of Patent: Oct. 9, 2012

(54) AGROCHEMICAL COMPOSITIONS CONTAINING NAPHTHALENE SULFONATE DERIVATIVES AND NITROGEN-CONTAINING SURFACTANTS

(75) Inventors: Karin Bergström, Hålta (SE); Christine Strandberg, Mölndal (SE)

(73) Assignee: Akzo Nobel N V, Arnhem (NL)

( * ) Notice: Subject to any disclaimer, the term of this patent is extended or adjusted under 35 U.S.C. 154(b) by 1204 days.

(21) Appl. No.: 11/912,215

(22) PCT Filed: Apr. 20, 2006

(86) PCT No.: PCT/EP2006/061712
§ 371 (c)(1),
(2), (4) Date: Jan. 3, 2008

(87) PCT Pub. No.: WO2006/111563
PCT Pub. Date: Oct. 26, 2006

(65) Prior Publication Data
US 2008/0207456 A1    Aug. 28, 2008

Related U.S. Application Data

(60) Provisional application No. 60/673,523, filed on Apr. 21, 2005.

(30) Foreign Application Priority Data

Apr. 21, 2005   (EP) .................................. 05103237

(51) Int. Cl.
*A01N 31/08* (2006.01)
*C07C 323/25* (2006.01)
*A01P 13/00* (2006.01)
*A01P 3/00* (2006.01)
*A01P 7/04* (2006.01)

(52) U.S. Cl. .......................... 504/350; 510/492; 514/506

(58) Field of Classification Search ................... 504/350
See application file for complete search history.

(56) References Cited

U.S. PATENT DOCUMENTS

| 4,997,471 A | 3/1991 | Mente |
| 5,516,747 A * | 5/1996 | Lachut ........................... 504/362 |
| 5,912,209 A * | 6/1999 | Kassebaum et al. .......... 504/206 |
| 2002/0099131 A1 * | 7/2002 | Herbert et al. ................ 524/547 |

FOREIGN PATENT DOCUMENTS

| EP | 1 064 844 A1 | 1/2001 |
| GB | 819035 | 8/1959 |
| WO | WO 02/19821 | 3/2002 |

OTHER PUBLICATIONS

International Search Report for International Application No. PCT/EP2006/061712, Jun. 2, 2006.

* cited by examiner

*Primary Examiner* — Richard Schnizer
*Assistant Examiner* — Audrea Buckley
(74) *Attorney, Agent, or Firm* — Norris McLaughlin & Marcus, P.A.

(57) ABSTRACT

The present invention relates to a composition comprising a) an anionic compound having wetting and dispersing properties selected from the group of a1) an alkyl naphthalene sulfonate, a2) a naphthalene sulfonate-formaldehyde condensate that may optionally be alkyl substituted and mixtures thereof, and b) a nitrogen-containing surfactant selected from the group consisting of alkylamine alkoxylates, alkylamidoamine alkoxylates, alkanolamides and their alkoxylates, alkylamidopropylamines, betaines, amino acids, or any mixtures thereof, wherein <the weight ratio between a) and b) is between 99.99:0.01 and 40:60 while> the molar amount of anionic sulfonate and, if any are present, carboxylate groups in the composition is in excess of the molar amount of nitrogen-containing groups. These compositions exhibit synergistic wetting properties as compared to the surface-active components taken alone. Further, the compositions also exhibit an increased rainfastness. The compositions can be used as a wetting agent and/or as an agent for increasing rainfastness in cleaning or agricultural formulations. The invention also relates to an agricultural formulation per se.

12 Claims, 1 Drawing Sheet

Fig 1. Sodium n-butyl naphthalene sulfonate (NaBNS): B
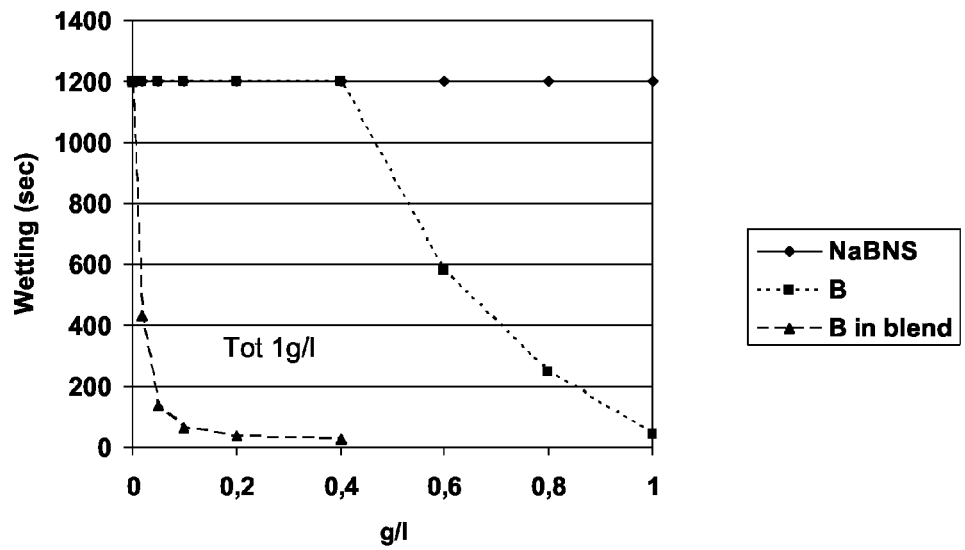
Fig 2. Sodium n-butyl naphthalene sulfonate (NaBNS): F
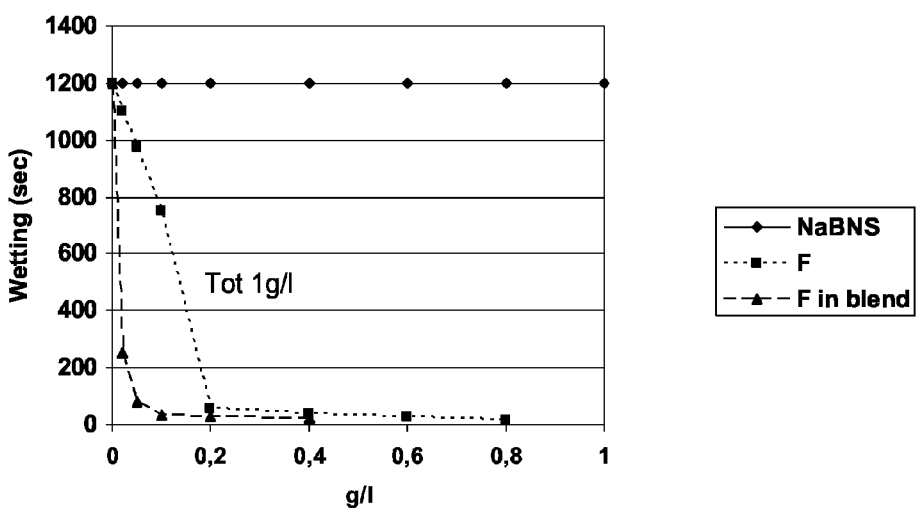

AGROCHEMICAL COMPOSITIONS CONTAINING NAPHTHALENE SULFONATE DERIVATIVES AND NITROGEN-CONTAINING SURFACTANTS

This case was filed under the Patent Cooperation Treaty on Apr. 20, 2006 and claims priority of European Application No. 05103237.3 filed on Apr. 21, 2005 and U.S. Provisional Application No. 60/673,523 filed on Apr. 21, 2005.

The present invention relates to compositions containing naphthalene sulfonate derivatives, such as alkyl naphthalene sulfonates and naphthalene sulfonate-formaldehyde condensates, optionally alkyl-substituted, and nitrogen-containing surfactants selected from the group consisting of alkylamine alkoxylates, alkylamidoamine alkoxylates, alkanolamides and their alkoxylates, alkylamidopropylamines, betaines, and amino acids, such as aminopropionates, iminopropionates, and glycinates, which compositions exhibit synergistic wetting properties as compared to the surface-active components taken alone. The compositions can be used as a wetting agent and/or as an agent for increasing rainfastness in cleaning or agricultural formulations. The invention also relates to an agricultural formulation per se, which in addition to the above-mentioned composition contains an agrochemical pesticide or another crop production chemical.

Wetting compositions normally contain different kinds of surfactants, such as anionic dispersants and/or anionic wetting agents, as well as agents to improve rainfastness. Frequently used good anionic dispersants with a high stabilizing effect are naphthalene sulfonate-formaldehyde condensates that are optionally alkyl substituted. Alkyl naphthalene sulfonates are examples of wetting agents that also exhibit stabilizing effects. However, it would be desirable to lower the total amount of chemicals in these compositions for economical and environmental reasons. When it comes to agricultural formulations, there is also the problem that the chemicals are too easily washed away when it rains or when the plants are being irrigated, and there is a need to increase the adsorption of the components of the formulations.

In U.S. Pat. No. 4,997,471 aqueous pesticide and latex paint compositions containing thickeners of the polyether type are described. The aqueous pesticide systems can further contain conventional additives such as wetting agents, anionic dispersants, and conventional nonionic surfactants. It is stated that nonionic surfactants can be added to increase or decrease the effectiveness of the thickeners. These nonionic surfactants can be, e.g., ethoxylates based on mono- or polyalkyl phenols, fatty acids, fatty amines, fatty amides or fatty alcohols. In the working examples the pesticide composition contains conventional wetting and dispersing agents, namely a sodium alkyl naphthalene sulfonate and a sodium salt of sulfonated naphthalene-formaldehyde condensate, respectively. In addition, a conventional nonionic, i.e. nonylphenol with 9 moles of ethylene oxide or an EO/PO block copolymer, and a thickener have been added.

WO 02/19821 relates to pesticidal formulations, especially aqueous suspensions of pesticides and pesticide mixtures. Naphthalene sulfonate/-formaldehyde condensates are claimed to be particularly suitable dispersing agents, and nonionic ethoxylated surfactants, such as condensation products of ethylene oxide with alcohols or with amines, are said to be particularly suitable bio-enhancing adjuvants. The preferred nonionic surfactants are alcohol ethoxylates from aliphatic alcohols having from 8 to 20 carbon atoms with 5-25, preferably 10-20 ethylene oxide units. In one particular aspect WO 02/19821 provides an aqueous suspension comprising 25% w/v of picoxystrobin (or a mixture of picoxystrobin and hexaconazole), one half the weight % of picoxystrobin (or one quarter to one half the weight % of the mixture) of a non-ionic ethoxylate surfactant, one tenth the weight % of picoxystrobin (or of the mixture) of a naphthalene sulphonate-formaldehyde condensate, 0.1 to 0.9% w/v of a non-ionic polymethyl methacrylate-polyethylene oxide graft copolymer, and 5 to 15% w/v of other additives, the remainder being water. In the working examples picoxystrobin and hexaconazole were present as active ingredients, naphthalene sulfonate/formaldehyde condensates as dispersants, and an ethoxylated fatty alcohol or ethoxylated sorbitan monolaurate as a nonionic bio-enhancing adjuvant.

In U.S. Pat. No. 5,516,747 surfactant mixtures of an alkyl naphthalene sulfonate and an alkyl polyglycoside, wherein the alkyl polyglycoside is present in an amount of 5-25% by weight of the surfactant mixture, are disclosed, as well as aqueous pesticide compositions containing the surfactant mixtures. These surfactant mixtures exhibit a surface tension which is lower than the expected value with regard to the individual values of the components.

In GB 819 035 mixed anionic-nonionic emulsifiers are disclosed, which are used in the preparation of readily emulsifiable oil concentrates. These concentrates are useful as cutting oils, as textile assistants, and as carriers for herbicides and insecticides for agricultural purposes. The anionic component is a salt of a sulfated hydroxyl compound containing at least one hydrocarbon chain of 8-18 carbon atoms, or a salt of a C8-C18 alkyl aryl sulfonic acid, e.g. calcium dinonyl naphthalene sulfonate, and the nonionic component is a fatty acid partial ester of a polyhydric alcohol, which may be ethoxylated, a fatty acid ester of a polyoxyethylene glycol, a fatty acid ester of a hexitol polyoxyethylene ether or an alcohol ether of a polyoxyethylene glycol having at least 12 carbon atoms in the alkyl group.

The main object of the present invention is to find a wetting composition with a high efficiency at a low total content of surfactants. Good wetting ability is of special interest for cleaning and agricultural applications. In the latter case also rainfastness is of particular interest. There is still a need for further improvement of the wetting properties to be able to reduce the total amount of chemicals present in the cleaning or agricultural formulations, and there is still a need for agrochemical formulations that are not so easily washed away from the leaves of plants.

Now it has surprisingly been found that this object is met by a composition comprising
a) an anionic compound having wetting and dispersing properties selected from the group of
  a1) an alkyl naphthalene sulfonate,
  a2) a naphthalene sulfonate-formaldehyde condensate that may optionally be alkyl substituted, and
  a3) mixtures thereof, and
b) a nitrogen-containing surfactant selected from the group consisting of alkylamine alkoxylates, alkylamidoamine alkoxylates, alkanolamides and their alkoxylates, alkylamidopropylamines, betaines, amino acids, and any mixtures thereof, wherein the molar amount of anionic sulfonate and, if any are present, carboxylate groups in the composition is in excess of the molar amount of nitrogen-containing groups.

This composition exhibits synergistic wetting properties as compared to the surface-active components taken alone, and in addition it has been found that the composition a)+b) also exhibits an increased rainfastness. Thus it has been found that for compositions containing the combination of a) the naphthalene sulfonate derivatives and b) the wetting agents, the amount adsorbed on a hydrophobic surface is larger as compared to a naphthalene sulfonate derivative alone. The adsorption is also stronger, so that when the surface is washed with water, the desorption time for the combination of a) and b) is longer than for the naphthalene sulfonate derivatives alone. Since the majority of leaf surfaces are hydrophobic, the results obtained from the hydrophobic model surface would be valid also for a hydrophobic leaf surface. The stronger adsorption and longer desorption times indicate that the combination of a) and b) will give rise to a better rainfastness of the composition than if a naphthalene sulfonate is used alone.

BRIEF DESCRIPTION OF THE DRAWINGS

The invention will now be described in greater detail with reference to the drawings, wherein:
FIG. 1 is a graph showing the wetting value for NaBNS:B compared to NaBNS and B separately; and
FIG. 2 is a graph showing the wetting value for NaBNS:F compared to NaBNS and F separately.

A further advantage of the present composition for use in agrochemical formulations is that it contains less inert materials, which in this context includes surface active components, raising the possibility of increasing the concentration of the pesticide in the formulation. Additionally, agrochemical suspension formulations comprising the present composition have an improved stability, and when these suspensions have settled, they are easier to redisperse.

The weight ratio between a) and b) is at most 99.99:0.01, preferably at most 99:1, more preferably at most 98:2, even more preferably at most 97:3, even more preferably still at most 96:4, and most preferably at most 95:5, and at least 40:60, preferably at least 50:50, more preferably at least 60:40, even more preferably at least 70:30, more preferably still at least 75:25, even more preferably still at least 80:20 and most preferably at least 85:15. Component a1 is mainly a wetting agent, but also has some dispersing ability, whereas a2 is mainly a dispersing agent and exhibits wetting properties to a minor extent. The nitrogen-containing surfactants of group b) are good wetting agents.

The above-mentioned composition can be advantageously used in an agricultural formulation which contains an agrochemical pesticide or another crop production chemical. For such an agricultural formulation the total amount of inert materials can be lowered while still retaining or improving the wetting properties of the formulation. It is preferred to have a minor amount of the nitrogen-containing surfactant in the composition, since the anionic compounds must be present in an amount that is still sufficient for them to exert their dispersing/stabilising ability. Also, a high concentration of nitrogen-containing surfactant could result in an agrochemical formulation that is phytotoxic. Taking these aspects into consideration, the molar amount of anionic sulfonate and carboxylate groups in the composition of the invention must be in excess of the molar amount of nitrogen-containing groups. It is noted that carboxylate groups are present when the nitrogen-containing compound is an amphoteric or zwitterionic compound selected from group b), such as an amino acid or a betaine.

The pesticides to be used in the compositions according to the invention can be solid or liquid at room temperature, and they can be either water- or organo-soluble. The pesticides can be herbicides, fungicides, insecticides, acaricides or other crop production chemicals, such as plant growth regulators and micronutrients. Suitable examples of herbicides are acetamides, ALS inhibitor compounds, amino acids such as glyphosate, carbamates, benzoic acids such as dicamba, dinitroanilines, benzofurans such as ethofumesate, hydroxy-benzonitriles such as bromoxynil and ioxynil, phenoxy acids, anilides such as propanil, triazines, and ureas such as diuron, fenuron, and metha-benzothiazuron. Suitable examples of fungicides are benzimidazoles such as carbendazim, members of the Multi-Site chemical class such as mancozeb, chlorothalonil, and copper octanoate, and strobilurins such as azoxystrobin and trifloxystrobin. Suitable examples of insecticides are oxadiazines such as indoxacarb, organochlorines, organophosphates, and pyrethroid. Suitable examples of acaricides are amidines such as amitraz, organophosphorus such as dimethoate, chlorpyrifos and ethion, pyrazoles such as chlorfenapyr, tetrazines such as clofentezine, organochlorines such as dicofol, and pyrethroids such as fenpropathrin.

The pesticide or crop production formulations according to the invention can be of different types. A composition may for example be formulated as
1) a wettable powder or in granular form
2) a suspension concentrate or
3) a suspo emulsion.

1) In conventional processes a wettable powder from a solid pesticide is typically prepared by applying the following procedures. The pesticide is finely ground and combined with an inert solid diluent such as kaolin, attapulgite clays or diatomaceous earth. The other ingredients, such as dispersants and wetting agents, are also mixed with the pesticide and the solid diluent before milling of the composition takes place. It is preferred that the surfactants used in the composition are also solid at the milling temperature, since this will make the milling procedure easier. The powders can be agglomerated into granules for more convenient handling. The wettable powders and granules based on solid, water-insoluble pesticides are added to water to form a suspension before the treatment. The amount of pesticide in the wettable powders or the granules ranges between 5 and 95, normally between 40 and 90% by weight of the total formulation, and may be present in an amount of up to 1,200 g/l, the amount of dispersant, such as a naphthalene sulfonate-formaldehyde condensate, normally is between 2 and 40, preferably 2 and 30, and most preferably 3 and 20% by weight of the total formulation, and the amount of wetting agent, such as an alkyl naphthalene sulfonate, is between 0.5 and 5% (w/w), the remainder being largely solid diluents and disintegration agents. The solid diluents thus can range from 0 to 92.5% by weight of the total formulation, normally from 0 to 40%. When naphthalene sulfonate-formaldehyde or alkyl naphthalene sulfonate-formaldehyde condensate is present, it acts both as a dispersant and a crystallization inhibitor, and also facilitates the disintegration of the granule. Granules can also be based on liquid pesticides, and the pesticides can be water-soluble or water-insoluble. For granules based on liquid pesticides, silica can be added for the adsorption of the pesticides. In these cases the pesticide can be present in a concentration of up to 50% by weight of the total formulation. Silica is a common example of a solid diluent that can be added to solid pesticides in an amount of around 1%, not more than 3%, to improve the flowable properties in the milling process and to facilitate disintegration of the granules.

The above process may be followed in the preparation of the wettable powders and granules according to the present invention. The wetting composition a+b is present in an amount of at least 1, preferably at least 2, and most preferably at least 3% by weight of the total formulation, and at most 40, preferably at most 30, and most preferably at most 20% by weight of the total composition.

2) Solid pesticides can also be formulated as a suspension concentrate, which can be based on water (for water-insoluble pesticides) or oil (for water-soluble pesticides). In conventional processes suspension concentrates are typically prepared by applying the following procedures. A solid pesticide is milled in a fluid medium, such as water or oil, in the presence of a dispersant and optionally a wetting agent. The pesticide is present in an amount of 4-90, preferably 10-80% by weight of the total formulation. If present, the concentration of wetting agent is 0.2-7, preferably 0.5-5% by weight of the total formulation.

The above process can be followed in the preparation of a suspension concentrate according to the invention. In the suspension concentrate the wetting composition a+b is preferably present in an amount of at least 1, preferably at least 2, and most preferably at least 2.5% by weight of the total formulation, and at most 20, more preferably at most 15, and most preferably at most 10% by weight of the total formulation. When a2 is present in the wetting composition, it will additionally act as dispersant for the solid pesticide.

3) Solid and liquid pesticides can also be used in a suspo emulsion. A suspo emulsion is the combination of a suspension concentrate and an emulsion concentrate. The composition according to the invention can also be used in this type of formulation.

All formulations can contain further wetting agents. Further, the formulations can also contain conventional additives such as anti-caking agents, anti-dusting agents, defoamers, anti-foamers, bactericides, preservatives, thickeners, adjuvants, antifreeze agents, and stabilizing agents, such as surfactants or polymers. Further ingredients in the water-dispersible granules can be silica and binding agents, such as starch and polyvinyl pyrrolidone. However, due to their high foaming properties, amine oxides preferably are not present in the formulations.

In all the above-mentioned types of compositions there is a need for a wetting agent which will make the aqueous emulsion or dispersion spread better on the target surface of, e.g., the leaves or on the soil. The wetting agent will also, in the case of wettable powders or granules, aid in the wetting of the dry components when water is added, and in the case of suspension concentrates it will aid in the wetting of the active ingredient when wet-milling.

As earlier stated, the wetting agent in the compositions of the present invention contains as necessary components a) an alkyl naphthalene sulfonate derivative and/or one or several of b) the nitrogen-containing surfactants mentioned. Surprisingly, the combinations of compounds b) and a) produce compositions where the wetting properties are far better than would be expected on the basis of the wetting of the individual components. Consequently, the total amount of wetting agent required to obtain a required wetting effect will be less when the combinations are used than when the components are used alone. Thus, a lower total amount of chemicals will be needed in the formulations, which is beneficial for the environment as well as less costly.

The alkyl naphthalene sulfonates to be used in the compositions preferably have alkyl groups with 1-10 carbon atoms, such as methyl, isopropyl, n-butyl, sec-butyl, and nonyl. Especially preferred products are sodium butyl naphthalene sulfonate and sodium nonyl naphthalene sulfonate. Examples of commercial alkyl naphthalene sulfonates are Morwet® B and Morwet IP.

The naphthalene sulfonate-formaldehyde condensate or alkyl naphthalene sulfonate-formaldehyde condensate to be used in the compositions preferably is a sodium salt having a mean molecular weight of 300 to 2,000, preferably 400 to 1,000 and most preferably 500-750. When present, the alkyl groups suitably contain 1-3 carbon atoms. An example of a suitable commercial condensate is Morwet D-425.

Preferred alkylamine alkoxylates, alkylamidoamine alkoxylates, and alkanolamides and their alkoxylates to be used in the composition have the following general formula

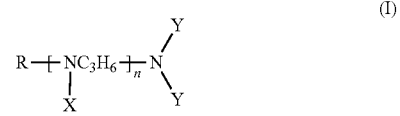

(I)

wherein R is a hydrocarbyl or an acyl group having 8-18, preferably 8-16, more preferably 8-14, and most preferably 10-14 carbon atoms, X is a hydrocarbyl group having 8-18, preferably 8-16, more preferably 8-14, and most preferably 10-14 carbon atoms, hydrogen, $(AO)_xH$ or the group

(II)

Y is hydrogen or $(AO)_xH$, n is 0-3, preferably 0-2, and most preferably 0-1, AO is an alkyleneoxy group with 2 or 3 carbon atoms, for ethyleneoxy groups $\Sigma x$ is 1-30, preferably 2-25, more preferably 2-20, and most preferably 2-15, for propyleneoxy groups $\Sigma x$ is 0-10, preferably 0-7, more preferably 0-5, even more preferably 0-3, and most preferably 0. The ethylene oxide and propylene oxide units can be added in blocks or randomly; when added in blocks, the ethylene oxide can be added first, followed by propylene oxide, or vice versa. The alkylamine alkoxylates can be derived from monoalkylamines, dialkylamines, alkylaminopropylamines, N,N-bis (3-aminopropyl)alkylamines, N-alkyl-N'-(3-aminopropyl)-1,3-propanediamines, N-(3-aminopropyl)-N'-[3-(alkylamino)propyl]-1,3-propanediamines, and alkylamidopropylamines.

Preferred alkanolamides or alkoxylated alkanolamides to be used in the composition have the formula

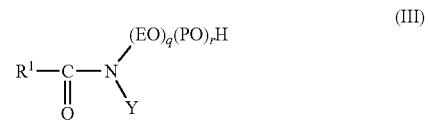

(III)

wherein $R^1(C=O)$— is an acyl group with 8-16, preferably 8-14, and most preferably 10-14 carbon atoms, Y is H or the group $(EO)_q(PO)_rH$, q is a number of 1-10 and the sum of all q is 1-20, preferably 1-15, and most preferably 1-10, r is 0-5 and the sum of all r is 0-10, preferably 0-5, and most preferably 0.

Preferred betaines to be used in the composition have the formula

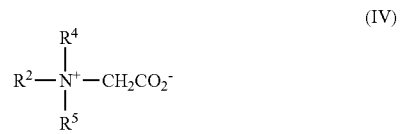

(IV)

wherein $R^2$ is a hydrocarbyl group with 8-18, preferably 8-16, more preferably 8-14, and most preferably 10-14 carbon atoms, or the group R³—C(=O)—NH—CH₂—CH₂—CH₂—, wherein R³—C(=O)— is an acyl group having 8-18, preferably 8-16, more preferably 8-14, and most preferably 10-14 carbon atoms, R⁴ and R⁵ are a C₁-C₄-alkyl group, preferably a C₁-C₂-alkyl group, and most preferably a methyl group, or the group (EO)ₛH, and s is a number of 1-10, preferably 1.

Preferred amino acids to be used in the composition have the formula

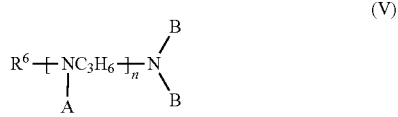

(V)

wherein R⁶ is a hydrocarbyl or acyl group with 8-18, preferably 8-16, more preferably 8-14, and most preferably 10-14 carbon atoms, n is a number of 0-3, preferably 0-2, and most preferably 0-1, A is a group —(CH₂)ₜ—CO₂⁻M⁺, hydrogen or the group

(VI)

and B is a group —(CH₂)ₜ—CO₂⁻M⁺ or H, provided that when R⁶ is an acyl group, n is at least 1 and the group A situated on the nitrogen atom bonded directly to the acyl group is hydrogen, t is a number 1-2, and M⁺ is a monovalent cation, such as Na⁺ or K⁺, at least one of the groups A and B is —(CH₂)ₜ—CO₂⁻M⁺.

Examples of compounds according to formula V are alkylamino propionates and alkylimino dipropionates, which are obtained by reacting an alkylamine with acrylic acid, and alkyl glycinates, which are obtained by reacting an alkylamine with sodium chloracetate.

Preferred alkylamidopropylamines to be used in the composition have the formula

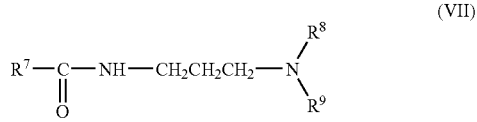

(VII)

wherein R⁷C(=O)— is an acyl group having 8-18, preferably 8-16, more preferably 8-14, and most preferably 10-14 carbon atoms, and R⁸ and R⁹ are, independently, an alkyl group with 1-4, preferably 1-2 carbon atoms. Most preferably, R⁸ and R⁹ is a methyl group. These latter compounds are typically obtained by reacting dimethylamino propylamine with a fatty acid.

The present invention is further illustrated by the following examples.

General

In the examples the following nitrogen-containing derivatives were used.

| Compound | Structure |
|---|---|
| A | Coco fatty amine ethoxylated with 2 moles of EO[1] |
| B | Coco fatty amine ethoxylated with 5 moles of EO |
| C | Coco fatty amine ethoxylated with 15 moles of EO |
| D | Tallow fatty amine ethoxylated with 5 moles of EO |
| E | Tallow fatty amine ethoxylated with 15 moles of EO |
| F | Coco alkyl monoethanolamide ethoxylated with 2 moles of EO |
| G | Coco alkyl monoethanolamide ethoxylated with 5 moles of EO |
| H | Coco fatty acid 3-(dimethylaminopropyl)amide |
| I | Sodium cocopropylenediamine tripropionate |
| J | N-(coco alkyl)diaminopropane with 3 moles of EO |
| K | Sodium cocoamphopolycarboxyglycinate (Sodium N,N,N'N''-tetracarboxymethyl coco dipropylenetriamine) |
| L | Coco amidopropyl dimethyl betaine |

[1]EO = ethylene oxide unit

EXAMPLE 1

The wetting properties and surface tension values of mixtures of sodium n-butyl naphthalene sulfonate having 29% alkylation on average and different nitrogen-containing wetting agents were investigated. The wetting was measured according to Drave's test (ASTM 02281), Alternative 2 and using the concentrations stated in the Table 1 for the respective compositions.

The surface tension values were obtained using the du Noüy ring (DIN 53914). The concentration of the solutions used for the surface tension measurements was 1 g/l.

TABLE 1

| Fatty amine derivative (FAD) in composition | Weight ratio Sodium n-butyl naphthalene sulfonate: FAD | Sodium n-butyl naphthalene sulfonate concentration g/l | FAD concentration g/l | Drave's wetting test sinking time (s) | Surface tension (mN/m) | pH |
|---|---|---|---|---|---|---|
| None | 100:0 | 1.0 | 0 | >1200 | 42 | 9.2 |
| A | 98:2 | 0.98 | 0.02 | 365 | 27 | |
| A | 95:5 | 0.95 | 0.05 | 160 | 27 | 8.9 |
| A | 90:10 | 0.90 | 0.10 | 104 | 28 | |
| A | 80:20 | 0.80 | 0.20 | 28 | 27.5 | |
| Pure A | 0:100 | | 1.00 | 100 | 31 | |
| B | 98:2 | 0.98 | 0.02 | 431 | 30 | |
| B | 95:5 | 0.95 | 0.05 | 139 | 29 | 9.6 |

TABLE 1-continued

| Fatty amine derivative (FAD) in composition | Weight ratio Sodium n-butyl naphthalene sulfonate: FAD | Sodium n-butyl naphthalene sulfonate concentration g/l | FAD concentration g/l | Drave's wetting test sinking time (s) | Surface tension (mN/m) | pH |
|---|---|---|---|---|---|---|
| B | 90:10 | 0.90 | 0.10 | 63 | 29 | |
| B | 80:20 | 0.80 | 0.20 | 36 | 29 | |
| B | 70:30 | 0.70 | 0.30 | 26 | 29.3 | |
| Pure B | 0:100 | | 0.10 | >1200 | 31 | 9.2 |
| Pure B | 0:100 | | 0.40 | >1200 | 31 | 9.1 |
| Pure B | 0:100 | | 0.60 | 580 | 31 | |
| Pure B | 0:100 | | 1.00 | 40 | 30 | |
| C | 98:2 | 0.98 | 0.02 | 678 | 32 | |
| C | 95:5 | 0.95 | 0.05 | 136 | 32 | 9.3 |
| C | 90:10 | 0.90 | 0.10 | 74 | 33 | |
| Pure C | 0:100 | | 1.00 | >600 | 38 | |
| D | 98:2 | 0.98 | 0.02 | >1200 | 34 | |
| D | 95:5 | 0.95 | 0.05 | 1020 | 32 | 9.3 |
| D | 90:10 | 0.90 | 0.10 | 377 | 37 | |
| D | 80:20 | 0.80 | 0.20 | 500 | 30.9 | |
| Pure D | 0:100 | | 0.20 | >1200 | 32.2 | |
| Pure D | 0:100 | | 1.0 | 80 | 31 | |
| E | 98:2 | 0.98 | 0.02 | >1200 | 35 | |
| E | 95:5 | 0.95 | 0.05 | 800 | 34 | 9.5 |
| E | 90:10 | 0.90 | 0.10 | 195 | 34 | |
| Pure E | 0:100 | | 1.0 | >600 | 39 | |
| F | 98:2 | 0.98 | 0.02 | 254 | 30 | |
| F | 95:5 | 0.95 | 0.05 | 80 | 29 | 8.3 |
| F | 90:10 | 0.90 | 0.10 | 36 | 27 | |
| F | 80:20 | 0.80 | 0.20 | 31 | 26 | |
| F | 70:30 | 0.70 | 0.30 | 25 | | |
| Pure F | 0:100 | | 0.10 | 750 | 28 | |
| Pure F | 0:100 | | 0.20 | 57 | 27 | 7.5 |
| Pure F | 0:100 | | 0.80 | 15 | 26 | |
| G | 95:5 | 0.95 | 0.05 | 260 | 31 | |
| G | 90:10 | 0.90 | 0.10 | 67 | 30 | |
| Pure G | 0:100 | | 0.10 | >1200 | 30.7 | 7.3 |
| Pure G | 0:100 | | 0.80 | 17 | 31 | |
| H | 98:2 | 0.98 | 0.02 | 440 | 30 | |
| H | 95:5 | 0.95 | 0.05 | 154 | 29 | |
| H | 90:10 | 0.90 | 0.10 | 86 | 29 | |
| Pure H | 0:100 | | 0.20 | >1200 | 29 | 9.7 |
| Pure H | 0:100 | | 1.0 | 75 | 27 | |
| I | 98:2 | 0.98 | 0.02 | 850 | 33 | |
| I | 95:5 | 0.95 | 0.05 | 170 | 30 | |
| I | 90:10 | 0.90 | 0.10 | 95 | 30 | |
| Pure I | 0:100 | | 0.30 | 300 | 39 | |
| J | 98:2 | 0.98 | 0.02 | >1200 | 31 | |
| J | 95:5 | 0.95 | 0.05 | 940 | 30 | 9.9 |
| J | 90:10 | 0.90 | 0.10 | 420 | 29 | |
| J | 80:20 | 0.80 | 0.20 | 75 | 29.6 | |
| Pure J | 0:100 | | 1.0 | 296 | 30 | |
| K | 95:5 | 0.95 | 0.05 | 540 | 37.5 | 8.8 |
| K | 90:10 | 0.90 | 0.10 | 255 | 33 | |
| K | 80:20 | 0.80 | 0.20 | 180 | 31 | |
| K | 70:30 | 0.70 | 0.30 | 120 | 29.7 | |
| K | 60:40 | 0.60 | 0.40 | 60 | 29.5 | |
| Pure K | 0:100 | | 0.40 | >1200 | 34.5 | |
| L | 90:10 | 0.90 | 0.10 | 96 | 30.6 | |
| L | 80:20 | 0.80 | 0.20 | 46 | 29.8 | |
| Pure L | 0:100 | | 0.20 | >1200 | 31 | |

In all compositions the wetting was lower than can be expected from the values of the pure compounds. For example, the composition sodium n-butyl naphthalene sulfonate:J with the weight ratio 80:20 exhibits better wetting (75 s) than pure J at a concentration of 1.0 g/l. This is further illustrated in FIGS. 1 and 2 showing the wetting values for NaBNS:B and NaBNS:F blends, respectively, as compared to pure sodium n-butyl naphthalene sulfonate and pure B and F, respectively, wherein the blends contain a total of 1 g/l of the combination of NaBNS and the respective amine derivative.

EXAMPLE 2

The wetting properties and surface tension values of mixtures of sodium methyl naphthalene sulfonate-formaldehyde condensate having a mean molecular weight of 700 (range of molecular weight c. 200-900) and coco fatty amine ethoxylated with 5 moles of ethylene oxide were investigated. The wetting was measured according to Drave's test and the surface tension values were obtained using the du Noüy ring. The concentration of the solutions used for the surface tension measurements was 1 g/l.

TABLE 2

| Fatty amine derivatives (FAD) | Weight ratio sodium naphthalene sulfonate - formaldehyde condensate: FAD | Sodium (alkyl) naphthalene sulfonate - formaldehyde condensate concentration g/l | FAD concentration g/l | Drave's wetting test sinking time (s) | Surface tension (mN/m) | pH |
|---|---|---|---|---|---|---|
| None | 100:0 | 1.0 | 0 | >1200 | | |
| None | 100:0 | 2.0 | 0 | >1200 | 57.8 | 8.7 |
| B | 95:5 | 0.95 | 0.05 | >1200 | 43.9 | 10 |
| B | 90:10 | 0.90 | 0.10 | >1200 | 41 | |
| B | 90:10 | 1.80 | 0.20 | 660 | 40 | |
| B | 80:20 | 1.60 | 0.40 | 217 | 35.6 | |
| B | 70:30 | 1.40 | 0.60 | 102 | 35 | |
| Pure B | 0:100 | | 0.10 | >1200 | 31 | 9.2 |
| Pure B | 0:100 | | 0.40 | >1200 | 31 | 9.1 |
| Pure B | 0:100 | | 0.60 | 580 | 31 | |
| Pure B | 0:100 | | 1.00 | 40 | 30 | |

These tests clearly show that there is a synergistic wetting effect for the composition of the invention. For example, the composition at 80:20 wherein B is present at a concentration of 0.40 g/l has a wetting of 217 s, whereas pure B at a concentration of 0.40 g/l has a wetting of >1200 s.

EXAMPLE 3

TABLE 3

Adsorption was measured by a Biacore instrument, based on Surface Plasmon Resonance technique[1]. The concentration used was two times CMC. The hydrophobic surfaces were prepared by $C_{16}$-thiol adsorption on a gold surface[2].

| Product | Adsorption | CMC | Desorption time | Adsorption after flushing |
|---|---|---|---|---|
| Sodium methyl naphthalene sulfonate - formaldehyde condensate | 1.1 mg/m2 | 27 g/l | 1300 sek | 0.4 mg/m2 |
| B | 1.4 mg/m2 | 0.08 g/l | 1000 sek | 0.7 mg/m2 |
| Sodium methyl naphthalene sulfonate - formaldehyde condensate/B 95:5 | 1.5 mg/m2 | 0.06 g/l | 3500 sek | 0.9 mg/m2 |

[1] Sigal, G. B., Marksich, M., Whitesides, G. M. Langmuir 1997, 13, 2749-2755.
[2] Ederth, T., Liedberg, B., Langmuir 2000, 16, 2177-2184.

These tests show that the mixture has a better adsorption to the surface and a slower desorption from the surface, and that a higher proportion of the mixture is left on the surface, than for each of the components taken alone.

This is a clear demonstration that the rainfastness will be improved by this system.

EXAMPLE 4A

Suspension concentrates (SC) were made consisting of the following components:
  40% terbuthylazine
  2.5% dispersant/wetting agent
  5% propylene glycol
  0.3% xanthan gum The formulations were homogenised and diluted 1:10 in tap water. The contact angle was determined on Para film and on Pelargonium leaves by measurements using a FTÅ 200 instrument (First Ten Ångstroms), equipped with a video camera and image analysis software. The contact angle after 60 sec is given.

TABLE 4A

| Dispersant/wetting agent | Contact angle on Para film | Contact angle on *Pelargonium* leaves |
|---|---|---|
| Na methyl naphthalene sulfonate formaldehyde condensate (NaNSC) (Comparison) | 74° | 62° |
| NaNSC/M* ratio 99.5:0.5 (Comparison) | 71° | 67° |
| NaNSC/B** ratio 99.5:0.5 | 69° | 53° |
| NaNSC/B ratio 95:5 | 58° | 44° |

*M = 2-propylheptanol ethoxylated with 8 moles of EO (a nonionic surfactant)
**B = Coco fatty amine ethoxylated with 5 moles of EO The contact angle is much lower for the formulations according to the invention than for the comparison formulations, which indicates a better wetting ability.

EXAMPLE 4B

Suspension concentrates (SC) were made consisting of the following components:
  40% terbuthylazine
  2.5% Na methyl naphthalene sulfonate-formaldehyde condensate (NaNSC)
  1% co-dispersant/wetting agent
  5% propylene glycol
  0.3% xanthan gum

TABLE 4B

| Co-dispersant/wetting agent | Contact angle on Para film | Contact angle on *Pelargonium* leaves |
|---|---|---|
| NaBNS (Comparison) | 61° | 47° |
| NaBNS/M* ratio 80:20 (Comparison) | 57° | 41° |
| NaBNS/B** ratio 80:20*** | 50° | 39° |

*M = 2-propylheptanol ethoxylated with 8 moles of EO (a nonionic surfactant)
**B = Coco fatty amine ethoxylated with 5 moles of EO
***The weight ratio of the sum of sodium methyl naphthalene sulfonate-formaldehyde condensate and sodium n-butyl naphthalene sulfonate (=a2 + a1) to coco fatty amine ethoxylated with 5 moles of EO (=b) is 94:6.

This example includes a comparison formulation containing a nonionic surfactant that is an alcohol ethoxylate.

The contact angle is lower for the formulation according to the invention than for the comparison formulations, which indicates a better wetting ability.

EXAMPLE 5

In this example the stability of Suspension Concentrates according to the invention was investigated.

Suspension concentrates (SC) were made consisting of the following components:
43% Atrazin
2.5% dispersant/wetting agent
5% propylene glycol
0.3% xanthan gum Atrazin, dispersant, and water were milled in a Dyno Mill, KDL type, to a particle size between 3 μm and 7 μm. Propylene glycol and xanthan gum were added to a viscosity of 700-1000 cp. The formulations were kept at 54° C. for 2 weeks and bleeding (separation of a clear top layer) and the redispersability properties were investigated. Bleeding was detected by a visual inspection of the sample. In the case of a clear top layer, the height is measured and is expressed as % of the total height of the sample. The lower the value, the more stable the dispersion is.

The redispersability was investigated by adding 2 g of the SC to 98 g of water in a 100 ml cylinder. The cylinders were inverted until homogeneous suspensions were obtained. The cylinders were then left for the suspension to settle. After 24 hours, the samples were inverted and the number of inversions needed for complete redispersion was recorded.

TABLE 5

| Dispersant/wetting agent | Bleeding (%) | No of Inversions |
|---|---|---|
| NaNSC (comparison) | 11 | 25 |
| NaNSC/F**** ratio 80:20 | 5 | 8 |

****F = Coco alkyl monoethanolamide ethoxylated with 2 moles of EO

From the measurements in Table 5 it is evident that the formulation containing a mixture of sodium methyl naphthalene sulfonate-formaldehyde condensate and coco alkyl monoethanolamide ethoxylated with 2 moles of EO, according to the invention, exhibits a better stability than the comparison formulation containing only sodium methyl naphthalene sulfonate-formaldehyde condensate as a dispersant/wetting agent. It is also easier to redisperse the formulation according to the invention than the comparison formulation.

The invention claimed is:

1. A composition comprising
a) a naphthalene sulfonate-formaldehyde condensate that may optionally be alkyl substituted, and mixtures thereof, and
b) a nitrogen-containing surfactant selected from the group consisting of alkylamine alkoxylates, alkylamidoamine alkoxylates, alkanolamides and their alkoxylates, alkylamido propylamines, betaines, amino acids, or any mixtures thereof,
wherein the weight ratio between a) and b) is between 99.99:0.01 and 85:15, provided that the molar amount of anionic sulfonate and, if any are present, carboxylate groups in the composition is in excess of the molar amount of nitrogen-containing groups.

2. A composition according to claim 1 wherein b) is an alkylamine alkoxylate, an alkylamidoamine alkoxylate, an alkanolamide, and/or an alkanolamide alkoxylate having the following formula

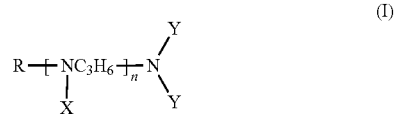

wherein R is a hydrocarbyl or an acyl group having 8-18 carbon atoms, X is a hydrocarbyl group having 8-18 carbon atoms, hydrogen, $(AO)_xH$ or the group

Y is hydrogen or $(AO)_xH$, n is 0-3, AO is an alkyleneoxy group with 2 or 3 carbon atoms, for ethyleneoxy groups the sum of x is 1-30, for propyleneoxy groups the sum of x is 0-10.

3. A composition according to claim 2 wherein b) is an alkanolamide or an alkoxylated alkanolamide according to the formula

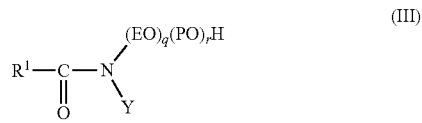

wherein $R_1C(=O)-$ is an acyl group with 8-16 carbon atoms, Y is H or the group $(EO)_q(PO)_rH$, where EO is an ethylene oxide group, each q is, independently, a number of 1-10 and the sum of all q is 1-20, each r is, independently, 0-5 and the sum of all r is 0-10.

4. A composition according to claim 1 wherein b) is a betaine having the formula

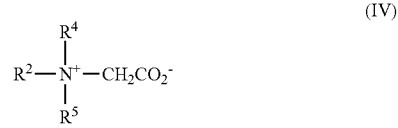

wherein $R^2$ is a hydrocarbyl group with 8-18 carbon atoms or the group $R^3-C(=O)-NH-CH_2-CH_2-CH_2-$, wherein $R^3-C(=O)-$ is an acyl group having 8-18 carbon atoms, $R^4$ and $R^5$ are a $C_1$-$C_4$-alkyl group or the group $(EO)_sH$, where EO is an ethylene oxide group and s is a number of 1-10.

5. A composition according to claim 1 wherein b) is an amino acid according to the formula

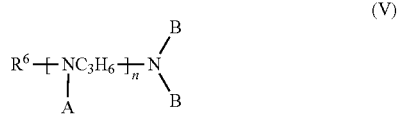

wherein $R^6$ is a hydrocarbyl or acyl group with 8-18 carbon atoms, n is a number of 0-3, A is a group $-(CH_2)_t-CO_2^-M^+$, hydrogen or the group

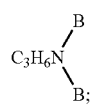
(VI)

and B is a group —$(CH_2)_t$—$CO_2^-M^+$ or H, provided that when $R^6$ is an acyl group, n is at least 1 and the group A situated on the nitrogen atom bonded directly to the acyl group is hydrogen, t is a number 1-2, and $M^+$ is a monovalent cation, at least one of the groups A and B is —$(CH_2)_t$—$CO_2^-M^+$.

6. A composition according to claim 1 wherein b) is an alkylamido propylamine having the formula

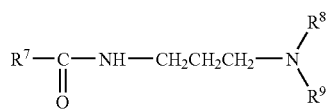
(VII)

wherein $R^7(C=O)$— is an acyl group having 8-18 carbon atoms and $R^8$ and $R^9$ are, independently, an alkyl group with 1-4 carbon atoms.

7. A composition according to claim 1 further comprising an agrochemical pesticide or another crop production chemical.

8. A composition according to claim 7 wherein the agrochemical pesticide or other crop production chemical is selected from the group consisting of herbicides, fungicides, insecticides, and fertilizers.

9. A wetting agent which comprises the composition of claim 1.

10. A cleaning composition comprising an effective amount of the composition of claim 1.

11. A composition according to claim 1 wherein the naphthalene sulfonate-formaldehyde condensate or optionally substituted alkyl naphthalene-sulfonate formaldehyde condensate has a mean molecular weight of 300-2,000, and wherein the alkyl group contains 1-3 carbon atoms.

12. A method for increasing the rainfastness of an agricultural formulation which comprises adding an effective amount therefor of the composition of claim 1 to said formulation.

* * * * *